United States Patent [19]

Grinwald

[11] Patent Number: 5,003,987

[45] Date of Patent: Apr. 2, 1991

[54] METHOD AND APPARATUS FOR ENHANCED DRUG PERMEATION OF SKIN

[76] Inventor: Paul M. Grinwald, 434 Balwyn Road, North Balwyn, Australia, 3104

[21] Appl. No.: 241,354

[22] Filed: Sep. 8, 1988

[30] Foreign Application Priority Data

Sep. 11, 1987 [AU] Australia ................................ PI4342
Nov. 25, 1987 [AU] Australia ................................ PI5676

[51] Int. Cl.[5] ................................................ A61B 5/05
[52] U.S. Cl. ..................................... 128/734; 128/639; 604/20
[58] Field of Search ............................... 128/639–641, 128/644, 636, 734; 604/20, 22, 289–290, 304; 324/57 R

[56] References Cited

U.S. PATENT DOCUMENTS

| | | | |
|---|---|---|---|
| 2,887,112 | 5/1959 | Smith | 128/644 |
| 3,834,374 | 9/1974 | Ensanian | 128/639 |
| 3,980,077 | 9/1976 | Shaw, IV | 128/639 X |
| 4,027,664 | 6/1977 | Heavner, Jr. et al. | 128/641 |
| 4,274,419 | 6/1981 | Tam et al. | 128/639 |
| 4,538,612 | 9/1985 | Patrick, Jr. | 128/639 X |
| 4,622,031 | 11/1986 | Sibalis | 604/20 |
| 4,769,022 | 9/1988 | Chang et al. | 604/289 X |
| 4,775,361 | 10/1988 | Jacques et al. | 604/20 |
| 4,778,457 | 10/1988 | York | 604/290 |
| 4,821,733 | 4/1989 | Peck | 128/636 |

Primary Examiner—Max Hindenburg

[57] ABSTRACT

A method and apparatus for preparation of a selected area of skin to facilitate drug absorption comprises removal of the outermost layers of the skin by gentle abrasion or other means, measuring the change in electrical resistance or impedance of the skin as the outermost layers of the skin are removed, and stopping skin removal when a predetermined optimum skin resistance or impedance is achieved to facilitate drug absorption. The preferred electrical resistance or impedance meter is in contact with the skin under consideration by two separate but adjacent conductive poles and is purpose calibrated to signal when the skin resistance or impedance level is such that rapid absorption of a drug will occur.

25 Claims, 2 Drawing Sheets

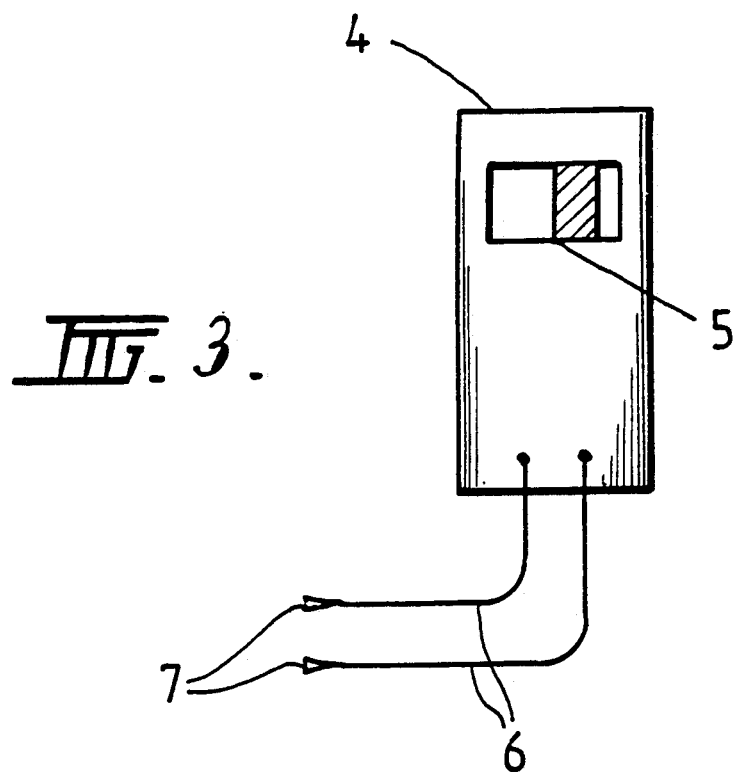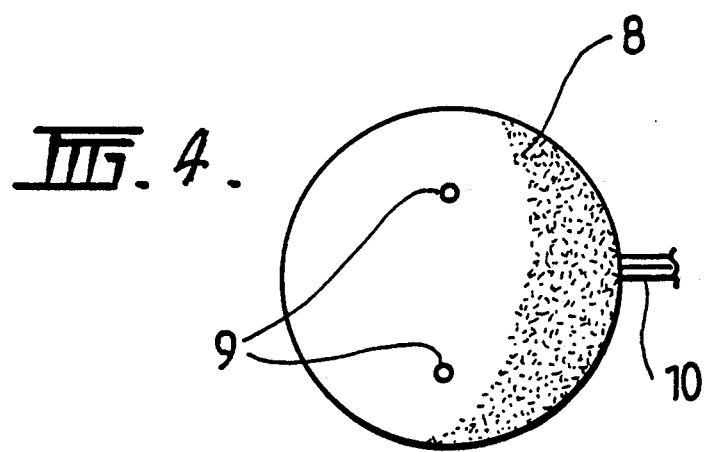

METHOD AND APPARATUS FOR ENHANCED DRUG PERMEATION OF SKIN

In summary, the object of the invention is to prepare a selected area of the skin of a patient for the purpose of facilitating drug absorption. The method comprises removal of the outermost layers of the skin by gentle abrasion or other means, measuring the change in electrical resistance or impedance of the skin as the outermost layers of the skin are removed, and stopping skin removal when a predetermined optimum skin resistance or impedance is achieved to facilitate drug absorption. Abrasion may be by wet or dry abrasion, and may be made manually or by electrically powered means, and is preferably carried out by use of disposable pads having fine abrasive material at the surface, and having a convex surface to provide access to the sometimes irregular contours of the body. The subject skin surface is preferably delimited by a target masking tape allowing selective exposure of the required portion of skin. The preferred electrical resistance or impedance meter is in contact with the subject skin by two separate but adjacent conductive poles and is purpose calibrated to signal when the skin resistance or impedance is such that rapid absorption of a drug will occur. Application of a local anaesthetic preparation will then lead to rapid spot anaesthesia, which is desirable prior to medical procedures requiring insertion of a needle. A detailed description follows below.

This invention relates generally to skin preparation and more particularly to a method and apparatus for enhancing drug permeation of skin.

The practice of needle insertion into the skin is common to many medical operations, for example, local anaesthesia, drug injection, blood sampling, etc. Common to all these procedures is the patient's discomfort of having a needle inserted into the skin. In order to alleviate this discomfort, it would desirable to produce spot anaesthesia of the skin prior to needle insertion. However, when drugs such as local anaesthetics are placed upon the skin, they are generally very poorly absorbed.

The epidermis (skin) acts as a physical and chemical barrier between the body and the environment. The epidermis contains numerous layers of cells, the cells in the outermost layers being filled with a horny substance called keratin. That the outermost layers of cells play an important role in the barrier mechanism was shown by an old observation. When adhesive tape is applied to the skin surface and then stripped away, the adhesive surface removes one layer of the outermost cornified cells. Repeated stripping with adhesive tape results in removal of all the cornified cells. Drugs such as local anaesthetics are then capable of penetrating the skin rapidly. Although this experiment was of considerable importance in shedding light on the barrier mechanism, it has not found general use as a practical method of enhancing drug penetration, no doubt because it is cumbersome and somewhat unpleasant.

In a different field of study, it is known to electrophysiologists that the quality of electrical recordings taken from body surface electrodes can be improved if the skin under the electrodes is lightly abraded before applying the electrodes. This reduces electrical noise by reducing the electrical impedance of the skin.

Abrasion is not practised as a means of skin preparation prior to drug application. The present applicant has found that abrasion results in uncontrolled and inconsistent amounts of removal of the outermost layers, so that drug penetration is not acheived, or alternatively that excessive cell removal with cell damage and irritation may occur. The present applicant has therefore conducted experiments in which the skin is abraded to various degrees, and the resultant change in electrical resistance is correlated with the ability of drugs to penetrate the skin so treated. Some results of these experiments may be summarised as follows. A small amount of abrasion initially produces a relatively large fall in skin resistance; further abrasion produces smaller decrements in the skin resistance. A small amount of abrasion produces a relatively large fall in resistance but insufficient improvement in permeation of drugs. With a moderate extent of abrasion, a range of electrical resistance is reached in which alcohol or concentrated (hyperosmotic) solutions placed on the skin are tolerated without discomfort (as with unabraded skin) and highly concentrated local anaesthetic solutions produce effective anaesthesia as judged by pain-free needle insertion within several minutes of applying the drug. However, low-concentration local anaesthetic solutions are ineffective. With a greater extent of abrasion, a lower range of electrical resistance is reached in which alcohol or concentrated solutions are not well tolerated due to discomfort on contact with the skin, and in which low-concentration local anaesthetic solutions are effective in producing local anaesthesia within a few minutes. Thus the range of electrical resistance reached provides a practical indication of the condition of the skin, such that rapid local anaesthesia is feasible provided that treatment appropriate to the resistance range is applied.

One object of the present invention is to provide a method and apparatus for skin preparation to facilitate the absorption of drugs.

Accordingly, the invention provides a method of skin preparation comprising the following steps:

(a) removing the outermost layers of the skin;

(b) measuring the change in electrical resistance or impedance of the skin as said outermost layers of the skin are removed; and, (c) stopping said skin removal when a predetermined optimum skin resistance or impedance is achieved to facilitate the absorbance of drugs.

The invention preferably provides a method wherein the electrical resistance is measured before and after removal of the outermost layers of skin.

The invention preferably provides intermittent or continuous resistance measurement as the skin is removed.

The invention preferably provides skin removal by abrasion.

The invention further provides skin removal by laser.

The invention further provides skin removal by shaving or cutting.

Preferably, the invention further provides measurement of the electrical resistance by a resistance or impedance meter having 2 poles in contact with the portion of the skin under consideration.

More preferably still, the invention provides abrasive removal of skin by an electrically powered moving pad having a fine abrasive material at its surface.

Preferably, the drug is an analgesic.

Another aspect of the present invention is an apparatus for use in preparing skin to facilitate the absorption of drugs.

DESCRIPTION OF DRAWINGS

FIG. 3 shows the resistance or impedance meter 4 with the measurement scale 5 calibrated to show the range of resistance or impedance required for successful drug application. The electrically conductive leads 6 connect the meter to the electrically conductive poles 7 which are placed on the skin for measurement.

FIG. 4 shows a pad of abrasive material 8 incorporating two electrically conductive areas 9 which are connected to leads 10 which provide connection to the resistance or impedance meter, for measurement of resistance or impedance during the abrasion process.

Figure 1:
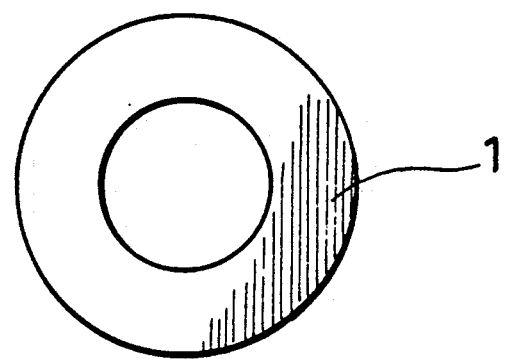
FIG. 1 shows the target masking tape 1 with central aperture.

Accordingly, the invention provides an apparatus for skin preparation comprising a skin removal means consisting of an abrasive material in the form of disposable pads incorporating two electrically conductive areas positioned in different parts of the pads for connection to a constant current electrical resistance or impedance meter.

The principle of the method is that the cornified layer of the epidermis has a high electrical resistance and hence its presence or absence can be detected by measurement of the electrical resistance of the skin. Removal of the cornified layer can cause the electrical resistance of the skin to decrease by a factor of several hundred fold. According to the invention, a method of removal of the outermost layer is used in conjuction with a device which measures the electrical resistance of the skin as the process of removal proceeds. When the electrical resistance has changed in the required manner, the device provides a signal or switches off the removal process.

For example, the method of removal may be by abrasion using an electrically powered moving pad having an abrasive material at its surface. The abrasive pad (8, FIG. 5) which is necessarily in contact with the skin is constructed with the inclusion of two electrically-conductive leads (9, FIG. 5) positioned in different parts of the pad so that each is in contact with the skin surface. Each lead makes connection (10, FIG. 5) with an instrument to measure the electrical resistance of the portion of skin at the surface of the pad between the two leads. As the abrasion commences, the resistance so measured will progressively fall from its normal initial value to a clearly lower value characteristic of skin with the major barrier function removed. The abrasive action is then halted by a switch triggered by occurrence of the electrical change.

Sensing of the electrical resistance can by made intermittently rather than continuously, and may alternate with small steps of further skin removal until the end-stage is reached as described.

The electrical resistance of the skin is sensed by a resistance meter (4, FIG. 3) having 2 poles (7, FIG. 3) in contact with the portion of the skin under consideration. These poles are small and closely adjacent but not touching. The readout (5, FIG. 3) of the instrument would, in general use, preferably not read in absolute units such as ohms, but would indicate whether or not a desired value suitable for the purpose had been attained. The indication could be by a light, by a needle reaching a distinct marking or by a dial graduated in time units i.e. showing what period of time should be allowed for drug application to produce anaesthesia on skin having resistance at the level reached. Since resistance readings from the skin are usually not immediately steady, the value reached after a standard time (1 second, 5 seconds, or other value) or the value projected to an extrapolated plateau could be the basis of the readout.

The meter may take the form of a constant current device (to limit the amount of current at low resistance, which can be uncomfortable). In this case, the voltage would be a measure of resistance.

The electrical impedance may be measured rather than the resistance. Alternatively other electrical properties based on these may be used.

The measuring device may have only one pole on the area of skin to be tested, the circuit being completed by a second pole on another portion of the body e.g. the palm of the hand.

The abrasive surface or device may be physically associated with the measuring instrument so as to provide intermittent or continuous readings as the abrasion proceeds, allowing termination of abrasion when the appropriate value has been reached. The abrasive process may be mechanically or electrically driven and terminated automatically when the appropriate skin condition is sensed.

Figure 2:
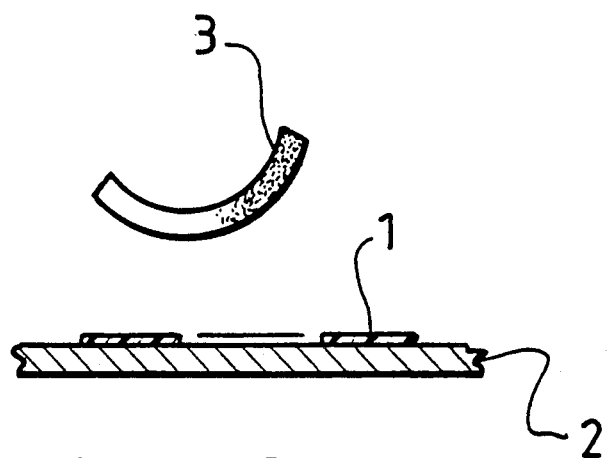
FIG. 2 shows the target masking tape 1 seen in section applied to the skin 2. The abrasive pad 3 on a curved surface is shown.

The abrasive article could be a fine grade of abrasive embedded in a small curved surface (3, FIG. 2) to provide access to the sometimes irregular contours of the body surface (2, FIG. 2), and should be produced economically enough to be disposable after a single use.

The area of skin to be abraded can be delimited by the application to the skin of a single use target masking tape consisting of a disc of adhesive backed tape (1, FIG. 1 and 1, FIG. 2) with a central aperture.

Removal of the skin layer may be by the action of a laser beam rather than by abrasion. In this case, the electrically-conductive terminals sensing resistance will preferably be transparent to the laser light, which would traverse the terminals placed in contact with the skin to ablate the surface layers beneath.

The conductors for any of the above may be metal, or metallized or carbon-impregnated materials, or aqueous solutions, or other materials. The abrasive material may be an electrically-conducting substance, or may have a conducting substance interspersed with it. Aqueous solutions may have a dye content to make visible the treated area of skin, preferably a dye which discriminates cornified versus non cornified cells. Solutions may also contain the drug to be applied, such as a local anaesthetic or other drug. The drug and/or dye may also be applied as a separate procedure, after completion of removal of the barrier layer.

The pharmaceutical vehicle containing the drug could take various forms, including a gel or self-adhesive gel, a lotion, paint or spray which is then applied to the abraded area. After a short time (usually 1 to 3 minutes or so), the skin anaesthesia produced is adequate for use of a needle in the ordinary way without discomfort.

Other agents could be employed rather than lignocaine e.g. drugs which are not local anaesthetics.

A dye could be included in the pharmaceutical formulation to assist in visual identification of the treated area. The dye should discriminate between cornified and non-cornified cells e.g. fluorescein, rose bengal.

The local anaesthetic agent or other drug or dye could be administered by iontophoretic means rather than by simple surface application to the abraded area.

As a result of the controlled removal of the major barrier layer of the epidermis, local anaesthetics or other drugs are able to permeate the skin much more rapidly than would otherwise be the case.

The invention is not necessarily restricted to the epidermis, but may be applied to any structure with a physically definable barrier layer.

Other objects, features and advantages of the present invention will become apparent from the following description of preferred embodiments.

The best method of performing the invention known to me is as follows.

A strip of adhesive tape with a central aperture 5 mm in diameter, is placed on the skin to isolate the area to be treated. An initial check is made of the electrical resistance of the selected area of skin, by applying the positive and negative terminals of the instrument. The terminals consist of metal poles 1 mm diameter, separated from each other by a distance of 1 mm. To carry out the resistance check, the skin is touched with paper tissue to ensure that the surface is dry, and the instrument terminals are moistened by touching to a pledget of cotton wool moistened with a mild detergent solution in water. After checking the resistance, the skin surface is made wet by a drop of fluid from the cotton wool pledget, and lightly abraded by passing fine-grain abrasive paper over it several times, ensuring that the skin remains wet while doing so. The abrasive paper is preferably attached by adhesive backing to the curved surface of a cylinder 3 cm diameter, so that the skin contacts the curved face of the paper and not its edges. The skin is then dried with the paper tissue, and a further instrument reading is taken in the same manner as before. If the reading is not in the required range indicated by the instrument, the skin is again moistened and further abraded, and this is repeated until the required reading is obtained. A drop of local anaesthetic solution is then applied. (paraffin oil saturated with lignocaine is suitable). The anaesthetic effect is then apparent after about 2 minutes.

An alternative method of performing the procedure is to make use of a dye, rather than electrical measurements, to recognise the stage at which the skin has been rendered permeable. Certain dyes, such as fluorescein stain viable cells, but not those which are cornified. Abrasion of the surface of the skin can be carried out followed by application of the dye solution. Removal of the dye solution with paper tissue then discloses whether the exposed surface has taken up the dye, and therefore whether it is adequately prepared for application of the local anaesthetic solution. Similarly, a dye which is selectively taken up by the cornified cells of the skin, but not by noncornified cells, could also be used in an analogous manner.

In some purposes it will be useful to include a dye in the formulation of the local anaesthetic application to give a visual indication that penetration has occurred, signalled by colour change accompanying transfer of the dye from the local anaesthetic solution to the skin. For example, the dye neutral red is yellow in its uncharged (oil-soluble) form, and red in its ionic (water-soluble) form. The local anaesthetic in an oil vehicle contains neutral red in its yellow state. After application to the skin, diffusion of the dye would impart a red appearance to the skin as it entered the skin and became ionised. Recognition of this colour development indicates that penetration of the dye has occurred, showing that the local anaesthetic would have penetrated to a proportional extent, and thus signalling that sufficient time has occurred to have produced an anaesthetic effect.

Methods of mechanical modification of the surface other than abrasion also come within the scope of this invention, including shaving or planing, in which a razor is drawn across the skin to remove the outermost layer, and multiple fine incision, in which a fine point is pressed or drawn repeatedly across the surface to produce discontinuities in the outer layer.

The claims defining the invention are as follows:

1. A method of skin preparation to facilitate absorption of drugs comprising the following steps:
   (a) removing the outermost layers of the skin;
   (b) measuring the change in electrical resistance or impedance of the skin as said outermost layers of the skin are removed; and,
   (c) stopping said skin removal when a predetermined optimum skin resistance or impedance is achieved to facilitate the absorption of drugs.

2. A method according to claim 1, wherein the electrical resistance or impedance is measured before and after removal of the outermost layers of the skin.

3. A method according to claim 1, wherein the electrical resistance or impedance is measured intermittently as the outermost layers of the skin are removed.

4. A method according to claim 3, wherein the measurement of electrical resistance or impedance is alternated with small steps of skin removal.

5. A method according to claim 1, wherein the electrical resistance or impedance is measured continuously as the outermost layers of the skin are removed.

6. A method according to any of claims 3, 4 or 5, wherein the measurement of electrical resistance or impedance is by resistance or impedance meter having two poles in contact with the portion of skin under consideration.

7. A method according to any of claims 3, 4 or 5, wherein the measurement of electrical resistance or impedance is by resistance or impedance meter having one pole in contact with the portion of skin under consideration and one pole in contact with another part of the body.

8. A method according to claim 1, wherein skin removal is by wet or dry abrasion.

9. A method according to claim 8, wherein removal of skin is by an electrically powered moving pad having fine abrasive materials at its surface.

10. A method according to claim 1, wherein skin removal is by shaving, cutting or other known means.

11. A method according to claim 1, wherein the skin is prepared for spot anaesthesia and the drug for absorption is a local anaesthetic.

12. A method according to claim 1 wherein the drug preparation contains a dye to signal by way of a colour change when the drug has penetrated the skin.

13. A method according to claim 1 wherein the drug preparation contains an oily vehicle and a dye to signal by way of a colour change corresponding to transition of the said dye from nonionic form within the oily vehicle to ionic form within the aqueous environment of the skin and indicting thereby when the drug preparation has penetrated the skin.

14. Apparatus for skin preparation to facilitate drug absorption comprising a skin removal means consisting of an abrasive material in the form of a pad incorporating two electrically conductive areas positioned in different parts of the pad for connection to an electrical resistance of impedance meter.

15. An apparatus according to claim 14 wherein the abrasive material is attached to a curved surface 3 cm in diameter.

16. A method of skin preparation to facilitate absorption of drugs comprising the following steps:
   (a) Removing the outermost layers of the skin by wet or dry abrasion, wherein skin removal is delimited by application to the skin of a single use target masking tape consisting of a disk of adhesive backed tape with a central aperture;
   (b) Measuring the change in electrical resistance or impedance of the skin as said outermost layers of the skin are removed; and,
   (c) Stopping said skin removal when a pre-determined optimum skin resistance or impedance is achieved to facilitate the absorption of drugs.

17. A method of skin preparation to facilitate absorption of drugs comprising the following steps:
   (a) Removing the outermost layers of the skin by an electrically powered moving pad having fine abrasive materials at its surface and wherein skin removal is delimited by application to the skin of single use target masking tape consisting of a disc of adhesive backed tape with a central aperture;
   (b) Measuring the change in electrical resistance or impedance of the skin as said outermost layers of the skin are removed; and,
   (c) Stopping said skin removal when a pre-determined optimum skin resistance or impedance is achieved to facilitate the absorption of drugs.

18. A method of skin preparation to facilitate absorption of drugs comprising the following steps:
   (a) Removing the outermost layers of the skin wherein skin removal is by Laser;
   (b) Measuring the change in electrical resistance or impedance of the skin as said outermost layers of the skin are removed; and,
   (c) Stopping said skin removal when a pre-determined optimum skin resistance or impedance is achieved to facilitate the absorption of drugs.

19. A method according to claim 18 wherein electrical resistance or impedance is measured by way of Laser transparent conductivity poles in contact with skin.

20. An electrical resistance or impedance meter with electrically conductive leads connected to a pair of electrically conductive poles so that the meter measures the electrical resistance or impedance when the said electrically conductive poles are applied in contact with the skin of a patient, wherein the said meter is calibrated to show the range of electrical resistance or impedance at which satisfactory drug effect will occur following application to the skin of a drug preparation of defined composition for a defined time.

21. An electrical resistance of impedance meter wherein the meter is calibrated according to claim 20, where the defined time of application is 2–3 and the drug preparation is a local anesthetic and the drug effect intended is local anesthesia of the skin to which the drug is applied.

22. An electrical resistance or impedance meter with electrically conductive leads connected to a pair of electrically conductive poles so that the meter measures the electrical resistance or impedance when the said electrically conductive poles are applied in contact with the skin of a patient, wherein the said meter is calibrated to show the range of electrical resistance or impedance at which satisfactory drug effect will occur following application to the skin of a local anaesthetic preparation of defined composition for less than three minutes.

23. Apparatus for skin preparation to facilitate absorption of drugs, said apparatus comprising in combination:
   (a) an electrical resistance or impedance meter with electrically conductive leads connected to a pair of electrically conductive poles,
   (b) said electrically conductive poles for application to the skin of a patient permitting measurement of electrical resistance or impedance, and
   (c) means of abrasion for abrasion of the said region of skin of a patient until a pre-determined skin resistance or impedance measurement is achieved to facilitate the absorption of drugs.

24. Apparatus for skin preparation to facilitate absorption of drugs, said apparatus comprising in combination:
   (a) an electrical resistance or impedance meter with electrically conductive leads connected to a pair of electrically conductive poles,
   (b) said electrically conductive poles for application to the skin of a patient permitting measurement of electrical resistance or impedance,
   (c) means of abrasion for abrasion of the said region of skin of a patient until a pre-determined skin resistance or impedance measurement is achieved to facilitate the absorption of drugs, and
   (d) a single use target masking tape consisting of a portion of adhesive backed tape with a central aperture for de-limiting the region of skin abrasion.

25. A method of skin preparation to facilitate absorption of drugs comprising the following steps:
   (a) removing the outermost layers of the skin by abrasion,
   (b) measuring the change in electrical resistance or impedance of the skin as said outermost layers of the skin are removed, and
   (c) stopping said skin removal when a pre-determined skin resistance or impedance is achieved to facilitate the absorption of drugs.

* * * * *